(12) United States Patent
Weiner et al.

(10) Patent No.: US 8,569,549 B2
(45) Date of Patent: *Oct. 29, 2013

(54) CATALYST SUPPORTS HAVING CRYSTALLINE SUPPORT MODIFIERS

(75) Inventors: Heiko Weiner, Pasadena, TX (US); Victor J. Johnston, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 363 days.

This patent is subject to a terminal disclaimer.

(21) Appl. No.: 13/018,615

(22) Filed: Feb. 1, 2011

(65) Prior Publication Data

US 2011/0257443 A1    Oct. 20, 2011

Related U.S. Application Data

(60) Provisional application No. 61/300,810, filed on Feb. 2, 2010.

(51) Int. Cl.
*C07C 29/149* (2006.01)
*C07C 31/00* (2006.01)
*B01J 23/00* (2006.01)

(52) U.S. Cl.
USPC .......................... 568/885; 502/254; 502/258

(58) Field of Classification Search
USPC ................................ 568/885; 502/254, 258
See application file for complete search history.

(56) References Cited

U.S. PATENT DOCUMENTS

| | | | |
|---|---|---|---|
| 2,021,698 A | 11/1935 | Perkins | |
| 2,105,540 A | 1/1938 | Lazier | |
| 2,607,807 A | 8/1952 | Ford | |
| 2,744,939 A | 5/1956 | Kennel | |
| 2,882,244 A | 4/1959 | Milton | |
| 3,130,007 A | 4/1964 | Breck | |
| 3,478,112 A | 11/1969 | Adam | |
| 3,702,886 A | 11/1972 | Araguer | |
| 3,729,429 A | 4/1973 | Robson | |
| 3,864,284 A | 2/1975 | Clippinger et al. | |
| 4,065,512 A | 12/1977 | Cares | |
| 4,228,307 A | 10/1980 | Zimmerschied | |
| 4,270,015 A | 5/1981 | Knifton | |
| 4,275,228 A | 6/1981 | Gruffaz | |
| 4,317,918 A | 3/1982 | Takano | |
| 4,328,373 A | 5/1982 | Strojny | |
| 4,337,351 A | 6/1982 | Larkins, Jr. | |
| 4,374,265 A | 2/1983 | Larkins, Jr. | |
| 4,395,576 A | 7/1983 | Kwantes | |
| 4,398,039 A | 8/1983 | Pesa | |
| 4,399,305 A | 8/1983 | Schreck | |
| 4,421,939 A | 12/1983 | Kiff | |
| 4,443,639 A | 4/1984 | Pesa | |
| 4,465,854 A | 8/1984 | Pond | |
| 4,471,136 A | 9/1984 | Larkins | |
| 4,480,115 A | 10/1984 | McGinnis | |
| 4,517,391 A | 5/1985 | Schuster | |
| 4,521,630 A | 6/1985 | Wattimena | |
| 4,550,185 A | 10/1985 | Mabry | |
| 4,581,473 A | 4/1986 | Polichnowski | |
| 4,613,700 A | 9/1986 | Maki | |
| 4,620,050 A | 10/1986 | Cognion | |
| 4,678,543 A | 7/1987 | Houben | |
| 4,692,218 A | 9/1987 | Houben | |
| 4,777,303 A | 10/1988 | Kitson | |
| 4,804,791 A | 2/1989 | Kitson | |
| 4,826,795 A | 5/1989 | Kitson | |
| 4,843,170 A | 6/1989 | Isshiki | |
| 4,886,905 A | 12/1989 | Larkins, Jr. | |
| 4,978,778 A | 12/1990 | Isshiki | |
| 4,985,572 A | 1/1991 | Kitson | |
| 4,990,655 A | 2/1991 | Kitson | |
| 5,061,671 A | 10/1991 | Kitson | |
| 5,137,861 A | 8/1992 | Shih | |
| 5,149,680 A | 9/1992 | Kitson | |
| 5,155,084 A | 10/1992 | Horn | |
| 5,185,308 A | 2/1993 | Bartley | |
| 5,241,106 A | 8/1993 | Inoue | |
| 5,243,095 A | 9/1993 | Roberts | |
| 5,306,845 A | 4/1994 | Yokohama | |
| 5,350,504 A | 9/1994 | Dessau | |
| 5,426,246 A | 6/1995 | Nagahara | |
| 5,475,144 A | 12/1995 | Watson | |
| 5,476,827 A | 12/1995 | Ferrero | |
| RE35,377 E | 11/1996 | Steinberg | |
| 5,585,523 A | 12/1996 | Weiguny | |
| 5,691,267 A | 11/1997 | Nicolau | |

(Continued)

FOREIGN PATENT DOCUMENTS

EP    0104197    4/1984
EP    0137749    4/1985

(Continued)

OTHER PUBLICATIONS

Alcala, et al., (2005). Experimental and DFT studies of the conversion of ethanol and acetic acid on PtSn-based catalysts, Journal of Physical Chemistry, 109(6), 2074-2085.

Brunauer Emmett and Teller, J. Am. Chem. Soc. 60, 309 (1938).

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Proc. Roy Soc. A314, pp. 473-498 (1970).

Rachmady, Acetic Acid Reduction by H2 on Bimetallic Pt" Fe Catalysts, Journal of Catalysis 209, 87-98 (Apr. 1, 2002), Elsevier Science (USA).

ZeaChem, Inc., Technology Overview, Lakewood, Colorado www.zeachem.com, 2008.

Zheng, et al. (2007). Preparation and catalytic properties of a bimetallic Sn-Pt complex in the supercages of NaY zeolite by use of surface organometallic chemistry, Applied Organometallic Chemistry, 21(10), 836-840.

(Continued)

*Primary Examiner* — Sikarl Witherspoon (57) ABSTRACT

A catalyst comprising a first metal, a silicaceous support, and at least one metasilicate support modifier, wherein at least 1 wt. % of the at least one metasilicate support modifier is crystalline in phase, as determined by x-ray diffraction. The invention also relates to processes for forming such catalysts, to supports used therein, and to processes for hydrogenating acetic acid in the presence of such catalysts.

9 Claims, 3 Drawing Sheets

(56) References Cited

U.S. PATENT DOCUMENTS

| | | |
|---|---|---|
| 5,719,315 A | 2/1998 | Tustin |
| 5,731,456 A | 3/1998 | Tustin |
| 5,767,307 A | 6/1998 | Ramprasad |
| 5,821,111 A | 10/1998 | Grady |
| 5,849,657 A | 12/1998 | Rotgerink |
| 5,861,530 A | 1/1999 | Atkins |
| 5,945,570 A | 8/1999 | Arhancet |
| 5,955,397 A | 9/1999 | Didillon |
| 5,973,193 A | 10/1999 | Crane |
| 6,040,474 A | 3/2000 | Jobson |
| 6,049,008 A | 4/2000 | Roberts |
| 6,093,845 A | 7/2000 | van Acker |
| 6,114,571 A | 9/2000 | Abel |
| 6,121,498 A | 9/2000 | Tustin |
| 6,232,352 B1 | 5/2001 | Vidalin |
| 6,232,504 B1 | 5/2001 | Barteau |
| 6,294,703 B1 | 9/2001 | Hara |
| 6,462,231 B1 | 10/2002 | Yanagawa |
| 6,472,555 B2 | 10/2002 | Choudary |
| 6,486,366 B1 | 11/2002 | Ostgard |
| 6,495,730 B1 | 12/2002 | Konishi |
| 6,509,180 B1 | 1/2003 | Verser |
| 6,509,290 B1 | 1/2003 | Vaughn |
| 6,559,333 B1 | 5/2003 | Brunelle |
| 6,603,038 B1 | 8/2003 | Hagemeyer |
| 6,632,330 B1 | 10/2003 | Colley |
| 6,670,490 B1 | 12/2003 | Campos et al. |
| 6,693,213 B1 | 2/2004 | Kolena |
| 6,696,596 B1 | 2/2004 | Herzog |
| 6,727,380 B2 | 4/2004 | Ellis |
| 6,765,110 B2 | 7/2004 | Warner |
| 6,768,021 B2 | 7/2004 | Horan |
| 6,812,372 B2 | 11/2004 | Janssen |
| 6,852,877 B1 | 2/2005 | Zeyss |
| 6,903,045 B2 | 6/2005 | Zoeller |
| 6,906,228 B2 | 6/2005 | Fischer |
| 6,927,048 B2 | 8/2005 | Verser |
| 7,074,603 B2 | 7/2006 | Verser |
| 7,084,312 B1 | 8/2006 | Huber |
| 7,297,236 B1 | 11/2007 | Vander Griend |
| 7,351,559 B2 | 4/2008 | Verser |
| 7,375,049 B2 | 5/2008 | Hayes |
| 7,425,657 B1 | 9/2008 | Elliott |
| 7,507,562 B2 | 3/2009 | Verser |
| 7,518,014 B2 | 4/2009 | Kimmich |
| 7,538,060 B2 | 5/2009 | Barnicki |
| 7,553,397 B1 | 6/2009 | Colley |
| 7,572,353 B1 | 8/2009 | Vander Griend |
| 7,601,865 B2 | 10/2009 | Verser |
| 7,608,744 B1 | 10/2009 | Johnston |
| 2003/0013908 A1 | 1/2003 | Horan |
| 2003/0077771 A1 | 4/2003 | Verser |
| 2003/0104587 A1 | 6/2003 | Verser |
| 2003/0114719 A1 | 6/2003 | Fischer |
| 2003/0191020 A1 | 10/2003 | Bharadwaj |
| 2004/0195084 A1 | 10/2004 | Hetherington |
| 2006/0019360 A1 | 1/2006 | Verser |
| 2006/0102520 A1 | 5/2006 | Lapinski |
| 2006/0106246 A1 | 5/2006 | Warner |
| 2006/0127999 A1 | 6/2006 | Verser |
| 2008/0207953 A1 | 8/2008 | Houssin |
| 2009/0005588 A1 | 1/2009 | Hassan |
| 2009/0023192 A1 | 1/2009 | Verser |
| 2009/0081749 A1 | 3/2009 | Verser |
| 2009/0166172 A1 | 7/2009 | Casey |
| 2009/0221725 A1 | 9/2009 | Chornet |
| 2009/0326080 A1 | 12/2009 | Chornet |
| 2010/0016454 A1 | 1/2010 | Gracey |
| 2010/0029995 A1 | 2/2010 | Johnston |
| 2010/0113843 A1 | 5/2010 | Lee |
| 2010/0121114 A1 | 5/2010 | Weiner |
| 2010/0168493 A1 | 7/2010 | LePeltier |
| 2010/0196789 A1 | 8/2010 | Fisher |
| 2010/0249479 A1 | 9/2010 | Berg-Slot |

FOREIGN PATENT DOCUMENTS

| | | |
|---|---|---|
| EP | 0167300 | 1/1986 |
| EP | 0175558 | 3/1986 |
| EP | 0192587 | 8/1986 |
| EP | 0285420 | 10/1988 |
| EP | 0330853 | 8/1989 |
| EP | 0372847 | 6/1990 |
| EP | 0408528 | 1/1991 |
| EP | 0198682 | 3/1991 |
| EP | 0285786 | 5/1993 |
| EP | 1277826 | 1/2003 |
| EP | 2060553 | 5/2009 |
| EP | 2060555 | 5/2009 |
| EP | 0400904 | 12/2009 |
| EP | 2186787 | 5/2010 |
| GB | 1168785 | 10/1969 |
| GB | 1559540 | 1/1980 |
| GB | 2136704 | 9/1984 |
| JP | 6-116182 A | 4/1994 |
| JP | 10306047 | 11/1998 |
| JP | 2001046874 | 2/2001 |
| JP | 2001157841 | 6/2001 |
| WO | 8303409 | 10/1983 |
| WO | 03040037 | 5/2003 |
| WO | 2009009322 | 1/2009 |
| WO | 2009009323 | 1/2009 |
| WO | 2009063176 | 5/2009 |
| WO | 2009105860 | 9/2009 |
| WO | 2010055285 | 5/2010 |

OTHER PUBLICATIONS

Pestman, et al., "A formation of keytones and aldehydes from carboxylic acids, structure-activity relationship for two competitive reactions," Journal of Molecular Catalysis A: Chemical, 103, 1995, pp. 175-180.

Pestman, et al., "Reactions of Carboxylic Acids on Oxides," Journal of Catalysts, 168, 1997, pp. 255-264.

Pestman et al., "Identification of the Active Sites in the Selective Hydrogenation of Acetic Acid to Acetaldehyde on Iron Oxide Catalysts," Journal of Catalysts, 174, 1998, pp. 142-152.

Santori, et al., "Hydrogenation of carbonylic compounds on Pt/SiO$_2$ catalysts modified with SnBu$_4$," Studies in Surface Science and Catalysis, 130, pp. 2063-2068, (2010).

Sarsfield et al., "Powder x-ray diffraction detection of crystalline phases in amorphous pharmaceuticals," Advances in x-ray analysis, International Centre for Diffraction Data, US v. 49, Jan. 1, 2006, pp. 322-327.

International Search Report and Written Opinion for PCT/US2011/023379 May 3, 2011.

Amit M. Goda et al., "DFT modeling of selective reduction of acetic acid to acetaldehyde on Pt-based bimetallic catalysts", 20th NAM, Houston, TX, Jun. 17-22, 2007.

International Preliminary Report on Patentability mailed Aug. 7, 2012 in corresponding International Application No. PCT/US2011/023379.

FIG. 1A - Selectivity Pt/Sn Catalyst

FIG. 1B - Productivity of Pt/Sn Catalyst

FIG. 1C - Conversion of HOAc

FIG. 2A - Selectivity of Re/Pd

FIG. 2B - Productivity of Re/Pd

FIG. 2C - Conversion of HOAc

US 8,569,549 B2

CATALYST SUPPORTS HAVING CRYSTALLINE SUPPORT MODIFIERS

CROSS-REFERENCE TO RELATED APPLICATION

This application claims priority to U.S. Provisional App. No. 61/300,810, filed Feb. 2, 2010, the entirety of which is incorporated herein by reference.

FIELD OF THE INVENTION

The present invention relates generally to supported catalysts comprising a crystalline support modifier for use, for example, in processes for hydrogenating acetic acid to form ethanol.

BACKGROUND OF THE INVENTION

There is a long felt need for economically viable processes and catalysts to convert acetic acid to ethanol which may be used in its own right or subsequently converted to ethylene which is an important commodity feedstock as it can be converted to polyethylene, vinyl acetate and/or ethyl acetate or any of a wide variety of other chemical products. Fluctuating natural gas and crude oil prices contribute to fluctuations in the cost of conventionally produced, petroleum or natural gas-sourced ethylene, making the need for alternative sources of ethylene all the greater when oil prices rise.

Catalytic processes for reducing alkanoic acids and other carbonyl group containing compounds have been widely studied, and a variety of combinations of catalysts, supports and operating conditions have been mentioned in the literature. The reduction of various carboxylic acids over metal oxides is reviewed by T. Yokoyama et al. in "Fine chemicals through heterogeneous catalysis. Carboxylic acids and derivatives." Chapter 8.3.1, summarizes some of the developmental efforts for hydrogenation catalysts for various carboxylic acids. (Yokoyama, T.; Setoyama, T. "Carboxylic acids and derivatives." in: "Fine chemicals through heterogeneous catalysis." 2001, 370-379.)

A series of studies by M. A. Vannice et al. concern the conversion of acetic acid over a variety of heterogeneous catalysts (Rachmady W.; Vannice, M. A.; *J. Catal.* (2002) Vol. 207, pg. 317-330.) The vapor-phase reduction of acetic acid by $H_2$ over both supported and unsupported iron was reported in a separate study. (Rachmady, W.; Vannice, M. A. *J. Catal.* (2002) Vol. 208, pg. 158-169.) Further information on catalyst surface species and organic intermediates is set forth in Rachmady, W.; Vannice, M. A., *J. Catal.* (2002) Vol. 208, pg. 170-179). Vapor-phase acetic acid hydrogenation was studied further over a family of supported Pt—Fe catalysts in Rachmady, W.; Vannice, M. A. *J. Catal.* (2002) Vol. 209, pg. 87-98) and Rachmady, W.; Vannice, M. A. *J. Catal.* (2000) Vol. 192, pg. 322-334).

Various related publications concerning the selective hydrogenation of unsaturated aldehydes may be found in (Djerboua, F.; Benachour, D.; Touroude, R. Applied Catalysis A: General 2005, 282, 123-133; Liberkova, K.; Tourounde, R. J. Mol. Catal. 2002, 180, 221-230.; Rodrigues, E. L.; Bueno, J. M. C. Applied Catalysis A: General 2004, 257, 210-211.; Ammari, F.; Lamotte, J.; Touroude, R. J. Catal. 2004, 221, 32-42; Ammari, F.; Milone, C.; Touroude, R. J. Catal. 2005, 235, 1-9.; Consonni, M.; Jokic, D.; Murzin, D. Y.; Touroude, R. J. Catal. 1999, 188, 165-175; Nitta, Y.; Ueno, K.; Imanaka, T.; Applied Catal. 1989, 56, 9-22.)

Studies reporting activity and selectivity over cobalt, platinum and tin-containing catalysts in the selective hydrogenation of crotonaldehyde to the unsaturated alcohol are found in R. Touroude et al. (Djerboua, F.; Benachour, D.; Touroude, R. Applied Catalysis A: General 2005, 282, 123-133 as well as Liberkova, K.; Tourounde, R.; *J. Mol. Catal.* 2002, 180, 221-230) as well as K. Lazar et al. (*Lazar, K.; Rhodes, W. D.; Borbath, I.; Hegedues, M.; Margitfalvi, 1. L. Hyperfine Interactions* 2002, 1391140, 87-96.)

M. Santiago et al. (Santiago, M. A. N.; Sanchez-Castillo, M. A.; Cortright, R. D.; Dumesic, 1. A. *J. Catal.* 2000, 193, 16-28) discuss microcalorimetric, infrared spectroscopic, and reaction kinetics measurements combined with quantum-chemical calculations.

Catalytic activity in for the acetic acid hydrogenation has also been reported for heterogeneous systems with rhenium and ruthenium. (*Ryashentseva, M. A.; Minachev, K. M.; Buiychev, B. M.; Ishchenko, V. M. Bull. Acad. Sci. USSR* 1988, 2436-2439).

U.S. Pat. No. 5,149,680 to Kitson et al. describes a process for the catalytic hydrogenation of carboxylic acids and their anhydrides to alcohols and/or esters utilizing platinum group metal alloy catalysts. U.S. Pat. No. 4,777,303 to Kitson et al. describes a process for the productions of alcohols by the hydrogenation of carboxylic acids. U.S. Pat. No. 4,804,791 to Kitson et al. describes another process for the production of alcohols by the hydrogenation of carboxylic acids. See also U.S. Pat. Nos. 5,061,671; 4,990,655; 4,985,572; and 4,826, 795.

In addition to the above-mentioned metals, catalysts, e.g., hydrogenation catalysts, have conventionally comprised a support material, and the support metal has been known to have an effect on the properties, e.g., performance properties, of the catalyst.

Malinowski et al. (*Bull. Soc. Chien. Belg.* (1985), 94(2), 93-5), discuss reaction catalysis of acetic acid on low-valent titanium heterogenized on support materials such as silica ($SiO_2$) or titania ($TiO_2$).

Bimetallic ruthenium-tin/silica catalysts have been prepared by reaction of tetrabutyl tin with ruthenium dioxide supported on silica. (Loessard et al., *Studies in Surface Science and Catalysis* (1989), *Volume Date* 1988, 48 (*Struct. React. Surf*), 591-600.)

The catalytic reduction of acetic acid has also been studied in, for instance, Hindermann et al., (Hindermann et al., *J. Chem. Res., Synopses* (1980), (11), 373), disclosing catalytic reduction of acetic acid on iron and on alkali-promoted iron.

The need remains, however, for novel hydrogenation catalysts that have high selectivity, conversion, and productivity to ethanol and having catalyst lifetimes that are suitable for commercial hydrogenation processes.

SUMMARY OF THE INVENTION

The present invention relates to catalysts useful for catalyzing the hydrogenation of acetic acid to ethanol. In a first embodiment, the invention is to a catalyst comprising a first metal, a silicaceous support, and at least one metasilicate support modifier, wherein at least 0.1 wt. %, e.g., at least 0.5 wt. %, at least 1 wt. %, at least 5 wt. %, at least 10 wt. %, at least 25 wt. %, at least 50 wt. %, at least 75 wt. %, at least 80 wt. %, at least 90 wt. %, of the metasilicate support modifier is in a crystalline phase, as determined by XRD. The catalysts of the invention beneficially may provide a productivity for ethanol in the hydrogenation of acetic acid of at least 800 grams per kilogram of catalyst per hour at high selectivity, e.g., a selectivity of at least 80%.

In another embodiment, the invention is to a process for producing ethanol, comprising hydrogenating acetic acid in the presence of a catalyst comprising a first metal, a silicaceous support, and at least one metasilicate support modifier, wherein at least 1 wt. % of the metasilicate support modifier is in a crystalline phase, as determined by XRD.

In preferred embodiments, the at least one metasilicate support modifier is selected from the group consisting of (i) alkaline earth metal metasilicates, (ii) alkali metal metasilicates, (iii) Group JIB metal metasilicates, (iv) Group IIIB metal metasilicates, and mixtures thereof. For example, the at least one metasilicate support modifier may be selected from metasilicates of a metal selected from the group consisting of sodium, potassium, magnesium, scandium, yttrium, and zinc. In a preferred embodiment, the at least one metasilicate support modifier comprises $CaSiO_3$. The at least one metasilicate support modifier preferably is present in an amount of 0.1 wt. % to 50 wt. %, based on the total weight of the catalyst.

The first metal optionally is selected from the group consisting of Group IB, JIB, IIIB, IVB, VB, VIIB, VIIB, or VIII transitional metal, a lanthanide metal, an actinide metal or a metal from any of Groups IIIA, IVA, VA, or VIA. For example, the first metal may be selected from the group consisting of copper, iron, cobalt, nickel, ruthenium, rhodium, palladium, osmium, iridium, platinum, titanium, zinc, chromium, rhenium, molybdenum, and tungsten. The first metal preferably is present in an amount of from 0.1 to 25 wt. %, based on the total weight of the catalyst.

The silicaceous support optionally is present in an amount of 25 wt. % to 99 wt. %, based on the total weight of the catalyst, and may have a surface area of from 50 $m^2$/g to 600 $m^2$/g. In preferred aspects, the silicaceous support is selected from the group consisting of silica, silica/alumina, calcium metasilicate, pyrogenic silica, high purity silica and mixtures thereof. The silicaceous support preferably contains less than 1 wt. % of aluminum, based on the total weight of the catalyst. In addition, the silicaceous support preferably contains less than 0.30 wt. % of the combination of aluminum oxide, titanium oxide and iron oxide, based on the total weight of the catalyst.

Optionally, the catalyst further comprises a second metal different from the first metal, e.g., a metal selected from the group consisting of copper, molybdenum, tin, chromium, iron, cobalt, vanadium, tungsten, palladium, platinum, lanthanum, cerium, manganese, ruthenium, rhenium, gold, and nickel. The second metal may be present in an amount of from 0.1 to 10 wt. %, based on the total weight of the catalyst. In a preferred aspect, the first metal is platinum and the second metal is tin, optionally at a molar ratio of platinum to tin is from 0.4:0.6 to 0.6:0.4. In another preferred aspect, the first metal is palladium and the second metal is rhenium, optionally at a molar ratio of rhenium to palladium is from 0.7:0.3 to 0.85:0.15.

The catalyst optionally further comprises a third metal different from the first metal and the second metal, e.g., wherein the third metal is selected from the group consisting of cobalt, palladium, ruthenium, copper, zinc, platinum, tin, and rhenium. The third metal optionally is present in an amount of 0.05 and 4 wt. %, based on the total weight of the catalyst.

The catalyst also preferably is suitable for use as a hydrogenation catalyst in converting acetic acid to ethanol and yields an acetic acid conversion of at least 10%. The catalyst preferably has a productivity that decreases less than 6% per 100 hours of catalyst usage.

In another embodiment, the invention is to a support for a hydrogenation catalyst, the support comprising, silicaceous support material; and a metasilicate support modifier, wherein at least 1 wt. % of the metasilicate support modifier is in a crystalline phase, as determined by XRD.

In another embodiment, the invention is to a process for preparing a catalyst, the process comprising the steps of: (a) contacting a first metal precursor to a first metal with a modified silicaceous support to form an impregnated support, wherein the modified silicaceous support comprises a silicaceous material and at least one metasilicate support modifier, the at least one metasilicate support modifier comprising at least 1 wt. % crystalline metasilicate, as determined by XRD; and (b) heating the impregnated support under conditions effective to reduce the first metal and form the catalyst. The process optionally further comprises contacting a second metal precursor to a second metal with the modified silicaceous support. In another aspect, the process further comprises the steps of: (c) contacting the at least one metasilicate support modifier or a precursor thereof with the silicaceous support to form a modified support precursor; and (d) heating the modified support precursor under conditions effective to form the modified silicaceous support.

BRIEF DESCRIPTION OF DRAWINGS

The invention is described in detail below with reference to the appended drawings, wherein like numerals designate similar parts.

DETAILED DESCRIPTION OF THE INVENTION

The present invention relates to catalysts for use in processes for producing ethanol by hydrogenating acetic acid. The hydrogenation of acetic acid to form ethanol may be represented by the following reaction:

The catalyst employed in the hydrogenation of acetic acid to form ethanol according to one embodiment of the invention comprises at least one metal, a support, e.g., a silicaceous support, and at least one metasilicate support modifier. Modified supports are discussed in U.S. Pub. No. 2010/0121114, which is hereby incorporated by reference in its entirety.

Surprisingly and unexpectedly, it has now been discovered that catalysts having supports that are modified, at least in part, with crystalline phase metasilicate support modifiers are particularly effective for forming ethanol in the hydrogenation of acetic acid, providing high conversions, selectivities and productivities for ethanol. According to some embodiments of the invention, for example, at least 0.5 wt. %, at least 1 wt. %, at least 2 wt. %, at least 3 wt. %, at least 5 wt. %, at least 10 wt. %, at least 25 wt. %, at least 50 wt. %, at least 75 wt. %, at least 80 wt. %, at least 90 wt. % or at least 95 wt. %, of the metasilicate support modifier is in a crystalline phase, as determined by X-Ray diffraction techniques (XRD). In terms of ranges the metasilicate support modifier is in a crystalline phase, as determined by XRD, may be from 0.5 wt. % to 99 wt. %, e.g., from 0.5 wt. % to 75 wt. %, 0.5 wt. % to 50 wt. %, 0.5 wt. % least 25 wt. %, from 0.5 wt. % to 10 wt. % or from 0.5 wt. % to 5 wt. %. In one embodiment, the metasilicate support modifier is in a crystalline phase, as determined by XRD, may be from 2 wt. % to 5 wt. %. Preferably the crystal system of the crystalline metasilicate is at least partially triclinic.

In various embodiments of the present invention, the crystalline character of the catalyst composition may be obtained from a substantially homogeneous crystalline metasilicate support modifier, meaning the metasilicate support modifier in substantially all of the catalyst particles has the same degree of crystallinity. In this aspect, the metasilicate support modifier in each of the catalyst particles the has a substantially uniform degree of crystallinity of at least 0.5 wt. %, at least 1 wt. %, at least 2 wt. %, at least 3 wt. %, at least 5 wt. %, at least 10 wt. %, at least 25 wt. %, at least 50 wt. %, at least 75 wt. %, at least 80 wt. %, at least 90 wt. % or at least 95 wt. %. In another aspect, the same overall degree of crystallinity may be achieved by blending a metasilicate support modifier that is crystalline to some degree, e.g., at least 5 wt. %, at least 10 wt. %, at least 25 wt. %, at least 50 wt. %, at least 75 wt. %, at least 80 wt. %, at least 90 wt. % or at least 95 wt. % crystalline as determined by XRD, with an amorphous or substantially amorphous metasilicate support modifier. The latter aspect may be desired to easily tune the degree of crystallinity of a catalyst batch to a desired crystallinity level.

As noted above, the catalyst of the present invention comprises, inter alfa, a support, e.g., a modified support, meaning a support that includes a support material and a support modifier, which adjusts the acidity of the support material. For example, the acid sites, e.g. Brønsted acid sites, on the support material may be adjusted by the support modifier to favor selectivity to ethanol during the hydrogenation of acetic acid. The acidity of the support material may be adjusted by reducing the number or reducing the availability of Brønsted acid sites on the support material. The support material may also be adjusted by having the support modifier change the pKa of the support material. Unless the context indicates otherwise, the acidity of a surface or the number of acid sites thereupon may be determined by the technique described in F. Delannay, Ed., "Characterization of Heterogeneous Catalysts"; Chapter III: Measurement of Acidity of Surfaces, p. 370-404; Marcel Dekker, Inc., N.Y. 1984, the entirety of which is incorporated herein by reference.

The support materials should be selected such that the catalyst system is suitably active, selective and robust under the process conditions employed for the formation of ethanol. Suitable support materials may include, for example, stable metal oxide-based supports or ceramic-based supports. Preferred support materials include silicaceous supports, such as silica, silica/alumina, a Group IIA silicate such as calcium metasilicate, pyrogenic silica, high purity silica and mixtures thereof. Other support materials may be used in some embodiments of the present invention, including without limitation, iron oxide, alumina, titania, zirconia, magnesium oxide, carbon, graphite, high surface area graphitized carbon, activated carbons, and mixtures thereof.

In addition, the support material is advantageously modified by a support modifier, e.g., a metasilicate support modifier, preferable calcium metasilicate. As indicated above, at least 0.5 wt. %, at least 1 wt. %, at least 2 wt. %, at least 3 wt. %, at least 5 wt. %, at least 10 wt. %, at least 25 wt. %, at least 50 wt. %, at least 75 wt. %, at least 80 wt. %, at least 90 wt. % or at least 95 wt. % of the metasilicate support modifier is in a crystalline phase, as determined by XRD. In terms of ranges, the amount of crystalline metasilicate support modifier in the support modifier may range, for example, from 1 wt. % to 75 wt. %, e.g., from 20 to 50 wt. %, from 40 to 70 wt. %, from 60 to 90 wt. %, or from 70 to 95 wt. %. By utilizing a high percentage of crystalline metasilicate in the support modifier, increases in productivity of ethanol (as compared to productivities obtained with comparable amorphous support modifiers) may be achieved. As one example, crystalline support modifiers may increase productivity by at least 5%, e.g., at least 10%, at least 15%, at least 20%, at least 30%, or at least 50%, over comparable amorphous metasilicate support modifiers. In terms of overall productivity, ethanol productivity of at least 500 grams of ethanol per kilogram catalyst per hour ("g/kg/hr"), e.g., at least 600 g/kg/hr, at least 700 g/kg/hr, at least 750 g/kg/hr, at least 800 g/kg/hr, at least 850 g/kg/hr, at least 900 g/kg/hr, or at least 1,000 g/kg/hr, may be achieved.

The modified support may also comprise impurities, examples of which include aluminum oxide, titanium oxide, and iron oxide. Surprisingly and unexpectedly, the inventors have found that significant improvements in ethanol productivity, selectivity, and/or conversion can be achieved with modified supports comprising particularly low levels of acidic impurities. In one embodiment, surprising and unexpected results are achieved when impurities, e.g., the combination of aluminum oxide, titanium oxide, and iron oxide, are present in an amount less than 0.30 wt. %, e.g., less than 0.20 wt. %, less than 0.15 wt. %, less than 0.13 wt. %, less than 0.10 wt. %, or less than 0.08 wt. %, based on the total weight of the catalyst.

In one embodiment, the support modifier has a low volatility or may be non-volatile. Low volatility modifiers have a rate of loss that is low enough such that the acidity of the support modifier is not reversed during the life of the catalyst. Such basic modifiers, for example, may be selected from the group consisting of: (i) alkaline earth oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used in embodiments of the present invention. Preferably, the support modifier is selected from the group consisting of oxides and metasilicates of any of sodium, potassium, magnesium, calcium, scandium, yttrium, and zinc, and mixtures of any of the foregoing. Preferably, the support modifier is a calcium silicate, more preferably calcium metasilicate ($CaSiO_3$), which is in crystalline phase, at least in part.

The total weight of the modified support, which includes the support material and the support modifier, based on the total weight of the catalyst, preferably is from 75 wt. % to 99.9 wt. %, e.g., from 78 wt. % to 97 wt. %, or from 80 wt. % to 95 wt. %. The support modifier preferably is provided in an amount sufficient to adjust the acidity, e.g., by reducing the number or reducing the availability of active Brønsted acid sites, and more preferably to ensure that the surface of the support is substantially free of active Brønsted acid sites. In preferred embodiments, the support modifier is present in an amount from 0.1 wt. % to 50 wt. %, e.g., from 0.2 wt. % to 25 wt. %, from 0.5 wt. % to 15 wt. %, or from 1 wt. % to 8 wt. %, based on the total weight of the catalyst. In preferred embodiments, the support material is present in an amount from 25 wt. % to 99 wt. %, e.g., from 30 wt. % to 97 wt. % or from 35 wt. % to 95 wt. %.

In one embodiment, the support material is a silicaceous support material selected from the group consisting of silica, silica/alumina, a Group IIA silicate such as calcium metasilicate, pyrogenic silica, high purity silica and mixtures thereof. Thus, in one aspect, the support material comprises calcium metasilicate, e.g., amorphous calcium metasilicate, and the support modifier comprises a metasilicate, which is crystalline, at least in part.

In the case where silica is used as the silicaceous support, it is beneficial to ensure that the amount of aluminum, which is a common contaminant for silica, is low, preferably under 1 wt. %, e.g., under 0.5 wt. % or under 0.3 wt. %, based on the total weight of the modified support. In this regard, pyrogenic silica is preferred as it commonly is available in purities exceeding 99.7 wt. %. High purity silica, as used throughout the application, refers to silica in which acidic contaminants such as aluminum are present, if at all, at levels of less than 0.3 wt. %, e.g., less than 0.2 wt. % or less than 0.1 wt. %. When calcium metasilicate, e.g., crystalline calcium metasilicate, is used as a support modifier, it is not necessary to be quite as strict about the purity of the silica used as the support material although aluminum remains undesirable and will not normally be added intentionally. The aluminum content of such silica, for example, may be less than 10 wt. %, e.g., less than 5 wt. % or less than 3 wt. %. In cases where the support comprises a support modifier in the range of from 2 wt. % to 10 wt. %, larger amount of acidic impurities, such as aluminum, can be tolerated so long as they are substantially counter-balanced by an appropriate amount of a support modifier.

The surface area of the support material, e.g., silicaceous support material, preferably is at least about 50 m$^2$/g, e.g., at least about 100 m$^2$/g, at least about 150 m$^2$/g, at least about 200 m$^2$/g or most preferably at least about 250 m$^2$/g. In terms of ranges, the support material preferably has a surface area of from 50 to 600 m$^2$/g, e.g., from 100 to 500 m$^2$/g or from 100 to 300 m$^2$/g. High surface area silica, as used throughout the application, refers to silica having a surface area of at least about 250 m$^2$/g. For purposes of the present specification, surface area refers to BET nitrogen surface area, meaning the surface area as determined by ASTM D6556-04, the entirety of which is incorporated herein by reference.

The support material also preferably has an average pore diameter of from 5 to 100 nm, e.g., from 5 to 30 nm, from 5 to 25 nm or from about 5 to 10 nm, as determined by mercury intrusion porosimetry, and an average pore volume of from 0.5 to 2.0 cm$^3$/g, e.g., from 0.7 to 1.5 cm$^3$/g or from about 0.8 to 1.3 cm$^3$/g, as determined by mercury intrusion porosimetry.

The morphology of the support material, and hence of the resulting catalyst composition, may vary widely. In some exemplary embodiments, the morphology of the support material and/or of the catalyst composition may be pellets, extrudates, spheres, spray dried microspheres, rings, pentarings, trilobes, quadrilobes, multi-lobal shapes, or flakes although cylindrical pellets are preferred. Preferably, the silicaceous support material has a morphology that allows for a packing density of from 0.1 to 1.0 g/cm$^3$, e.g., from 0.2 to 0.9 g/cm$^3$ or from 0.5 to 0.8 g/cm$^3$. In terms of size, the silica support material preferably has an average particle size, e.g., meaning the diameter for spherical particles or equivalent spherical diameter for non-spherical particles, of from 0.01 to 1.0 cm, e.g., from 0.1 to 0.5 cm or from 0.2 to 0.4 cm. Since the one or more metal(s) that are disposed on or within the modified support are generally very small in size, they should not substantially impact the size of the overall catalyst particles. Thus, the above particle sizes generally apply to both the size of the modified supports as well as to the final catalyst particles.

A preferred silica support material is SS61138 High Surface Area (HSA) Silica Catalyst Carrier from Saint Gobain N or Pro. The Saint-Gobain N or Pro SS61138 silica contains approximately 95 wt. % high surface area silica; a surface area of about 250 m$^2$/g; a median pore diameter of about 12 nm; an average pore volume of about 1.0 cm$^3$/g as measured by mercury intrusion porosimetry and a packing density of about 0.352 g/cm$^3$ (22 lb/ft$^3$).

A preferred silica/alumina support material is KA-160 (Sud Chemie) silica spheres having a nominal diameter of about 5 mm, a density of about 0.562 g/ml, in absorptivity of about 0.583 g H$_2$O/g support, a surface area of about 160 to 175 m$^2$/g, and a pore volume of about 0.68 ml/g.

One possible byproduct of the hydrogenation of acetic acid is ethyl acetate. According to the present invention, the support preferably includes a support modifier that is effective to suppress production of ethyl acetate, rendering the catalyst composition highly selective to ethanol. Thus, the catalyst composition preferably has a low selectivity toward conversion of acetic acid to ethyl acetate and highly undesirable by-products such as alkanes. The acidity of the support preferably is controlled such that less than 4%, preferably less than 2% and most preferably less than about 1% of the acetic acid is converted to methane, ethane and carbon dioxide. In addition, the acidity of the support may be controlled by using a pyrogenic silica or high purity silica as discussed above.

In one embodiment, the modified support comprises a support material and calcium metasilicate, including crystalline calcium metasilicate at least in part, as support modifier in an amount effective to balance Brønsted acid sites resulting, for example, from residual alumina in the silica. Preferably, the calcium metasilicate, e.g., crystalline calcium metasilicate, is present in an amount from 1 wt. % to 10 wt. %, e.g., from 4 to 8 wt. %, from 5 wt. % to 7 wt. %, or about 6 wt. %, based on the total weight of the catalyst, in order to ensure that the support is essentially neutral or basic in character.

As the support modifier, e.g., crystalline calcium metasilicate, may tend to have a lower surface area than the support material, e.g., silicaceous support material, in one embodiment the support material comprises a silicaceous support material that includes at least about 80 wt. %, e.g., at least about 85 wt. % or at least about 90 wt. %, high surface area silica in order to counteract this effect of including a support modifier.

Accordingly, without being bound by theory, modification and stabilization of oxidic support materials for the catalysts of the present invention by incorporation of non-volatile support modifiers having either the effect of: counteracting acid sites present upon the support surface or the effect of thermally stabilizing the surface makes it possible to achieve desirable improvements in selectivity to ethanol, prolonged catalyst life, or both. In general, support modifiers based on oxides in their most stable valence state will have low vapor pressures and thus have low volatility or are rather non-volatile. Accordingly, it is preferred that the support modifiers are provided in amounts sufficient to: (i) counteract acidic sites present on the surface of the support material; (ii) impart resistance to shape change under hydrogenation temperatures; or (iii) both. Without being bound by theory, imparting resistance to shape change refers to imparting resistance, for example, to sintering, grain growth, grain boundary migration, migration of defects and dislocations, plastic deformation and/or other temperature induced changes in microstructure.

Catalysts of the present invention are particulate catalysts in the sense that, rather than being impregnated in a wash coat onto a monolithic carrier similar to automotive catalysts and diesel soot trap devices, the catalysts of the invention preferably are formed into particles, sometimes also referred to as beads or pellets, having any of a variety of shapes and the catalytic metals are provided to the reaction zone by placing a large number of these shaped catalysts in the reactor. Commonly encountered shapes include extrudates of arbitrary cross-section taking the form of a generalized cylinder in the sense that the generators defining the surface of the extrudate are parallel lines. As indicated above, any convenient particle shape including pellets, extrudates, spheres, spray dried microspheres, rings, pentarings, trilobes, quadrilobes and multi-lobal shapes may be used, although cylindrical pellets are preferred. Typically, the shapes are chosen empirically based upon perceived ability to contact the vapor phase with the catalytic agents effectively.

One advantage of catalysts of the present invention is the stability or activity of the catalyst for producing ethanol. Accordingly, it can be appreciated that the catalysts of the present invention are fully capable of being used in commercial scale industrial applications for hydrogenation of acetic acid, particularly in the production of ethanol. In particular, it is possible to achieve such a degree of stability such that catalyst activity will have rate of productivity decline that is less than 6% per 100 hours of catalyst usage, e.g., less than 3% per 100 hours or less than 1.5% per 100 hours. Preferably, the rate of productivity decline is determined once the catalyst has achieved steady-state conditions.

In one embodiment, when the catalyst support comprises high purity silica, with crystalline calcium metasilicate, at least in part, as a support modifier, the catalyst activity may extend or stabilize, the productivity and selectivity of the catalyst for prolonged periods extending into over one week, over two weeks, and even months, of commercially viable operation in the presence of acetic acid vapor at temperatures of 125° C. to 350° C. at space velocities of greater than 2500 $hr^{-1}$.

In addition to the modified support material, the catalyst of the invention further comprises a first metal and optionally one or more of a second metal, a third metal or additional metals on the support. In this context, the numerical terms "first," "second," "third," etc., when used to modify the word "metal," are meant to indicate that the respective metals are different from one another. The total weight of all supported metals present in the catalyst preferably is from 0.1 to 25 wt. %, e.g., from 0.1 to 15 wt. %, or from 0.1 wt. % to 10 wt. %. For purposes of the present specification, unless otherwise indicated, weight percent is based on the total weight the catalyst including metal and support. The metal(s) in the catalyst may be present in the form of one or more metal oxides. For purposes of determining the weight percent of the metal(s) in the catalyst, the weight of any oxygen that is bound to the metal is ignored.

The first metal may be a Group IB, IIB, IIIB, IVB, VB, VIIB, VIIB, or VIII transitional metal, a lanthanide metal, an actinide metal or a metal from any of Groups IIIA, IVA, VA, or VIA. In a preferred embodiment, the first metal is selected the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium. More preferably, the first metal is selected from platinum and palladium. When the first metal comprises platinum, it is preferred that the catalyst comprises platinum in an amount less than 5 wt. %, e.g., less than 3 wt. % or less than 1 wt. %, due to the availability of platinum.

As indicated above, the catalyst optionally further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel. More preferably, the second metal is selected from tin and rhenium.

Where the catalyst includes two or more metals, one metal may act as a promoter metal and the other metal is the main metal. For instance, with a platinum/tin catalyst, platinum may be considered to be the main metal and tin may be considered the promoter metal. For convenience, the present specification refers to the first metal as the primary catalyst and the second metal (and optional metals) as the promoter(s). This should not be taken as an indication of the underlying mechanism of the catalytic activity.

If the catalyst includes two or more metals, e.g., a first metal and a second metal, the first metal optionally is present in the catalyst in an amount from 0.1 to 10 wt. %, e.g., from 0.1 to 5 wt. %, or from 0.1 to 3 wt. %. The second metal preferably is present in an amount from 0.1 and 20 wt. %, e.g., from 0.1 to 10 wt. %, or from 0.1 to 5 wt. %. For catalysts comprising two or more metals, the two or more metals may be alloyed with one another or may comprise a non-alloyed metal solution or mixture.

Figure 1A:
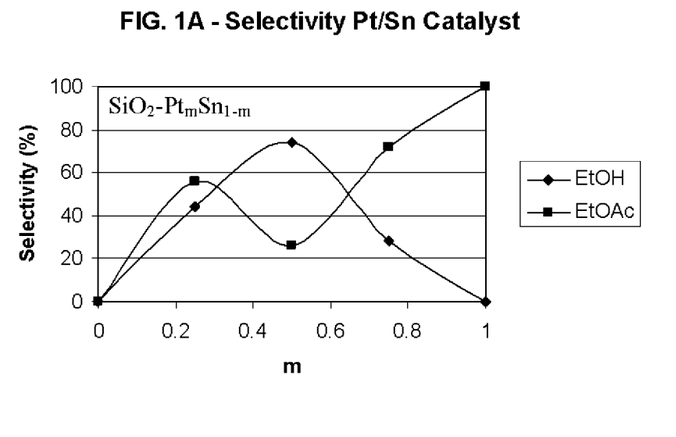
FIG. 1A is a graph of the selectivity to ethanol and ethyl acetate using a $SiO_2$—$Pt_mSn_{1-m}$ catalyst.
Figure 1B:
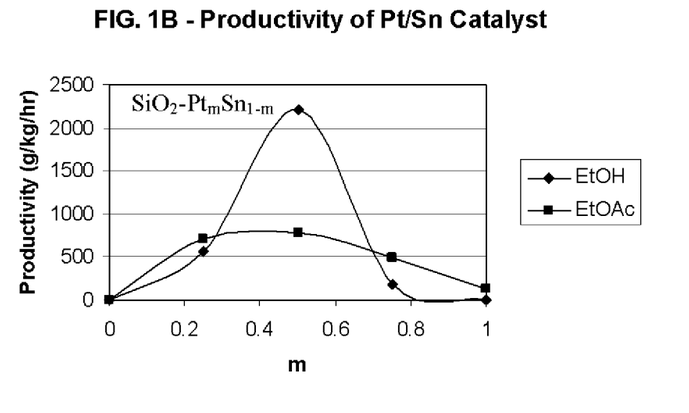
FIG. 1B is a graph of the productivity to ethanol and ethyl acetate of the catalyst of FIG. 1A.
Figure 1C:
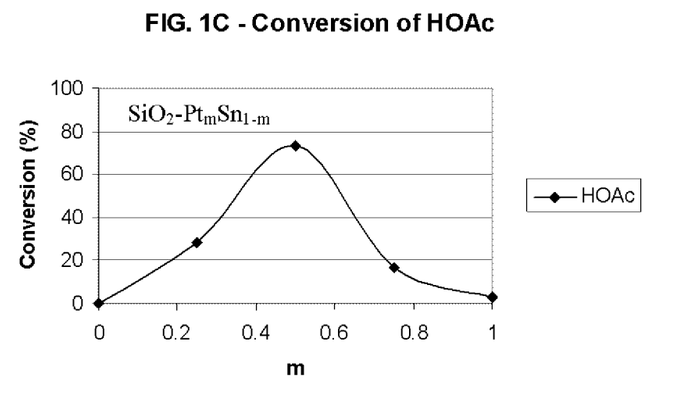
FIG. 1C is a graph of the conversion of the acetic acid of the catalyst of FIG. 1A.

The preferred metal ratios may vary somewhat depending on the metals used in the catalyst. In some embodiments, the mole ratio of the first metal to the second metal preferably is from 10:1 to 1:10, e.g., from 4:1 to 1:4, from 2:1 to 1:2, from 1.5:1 to 1:1.5 or from 1.1:1 to 1:1.1. It has now surprisingly and unexpectedly been discovered that for platinum/tin catalysts, platinum to tin molar ratios on the order of from 0.4:0.6 to 0.6:0.4 (or about 1:1) are particularly preferred in order to form ethanol from acetic acid at high selectivity, conversion and productivity, as shown in FIGS. 1A, 1B and 1C. Selectivity to ethanol may be further improved by incorporating modified supports as described herein.

Figure 2A:
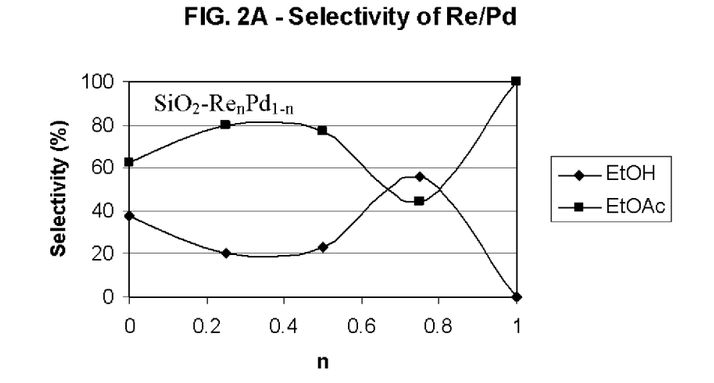
FIG. 2A is a graph of the selectivity to ethanol and ethyl acetate using a $SiO_2$—$Re_nPd_{1-n}$ catalyst.
Figure 2B:
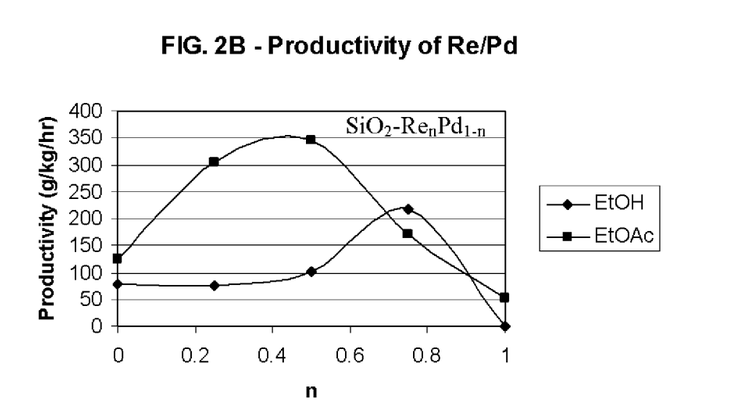
FIG. 2B is a graph of the productivity to ethanol and ethyl acetate of the catalyst of FIG. 2A.
Figure 2C:
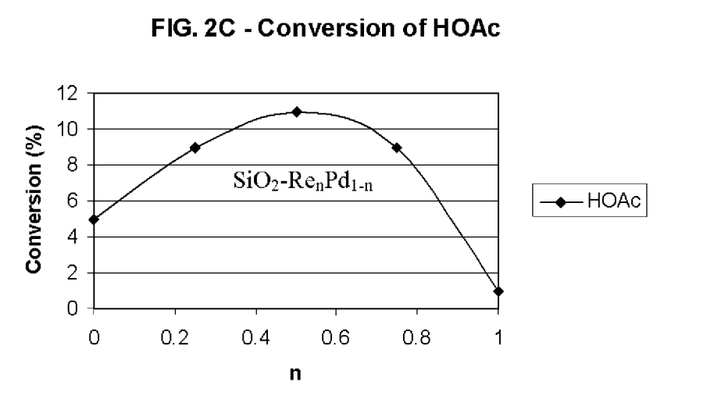
FIG. 2C is a graph of the conversion of the acetic acid of the catalyst of FIG. 2A.

Molar ratios other than 1:1 may be preferred for catalysts comprising different metals. With rhenium/palladium catalysts, for example, higher ethanol selectivities may be achieved at higher rhenium loadings than palladium loadings. As shown in FIGS. 2A, 2B and 2C, preferred rhenium to palladium molar ratios for forming ethanol in terms of selectivity, conversion and production are on the order of 0.7:0.3 to 0.85:0.15, or about 0.75:0.25 (3:1). Again, selectivity to ethanol may be further improved by incorporating modified supports as described herein.

In embodiments when the catalyst comprises a third metal, the third metal may be selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. More preferably, the second metal is selected from cobalt, palladium, and ruthenium.

When present, the total weight of the third metal preferably is from 0.05 and 4 wt. %, e.g., from 0.1 to 3 wt. %, or from 0.1 to 2 wt. %.

In one embodiment, the catalyst comprises a first metal and no additional metals (no second metal, etc.). In this embodiment, the first metal preferably is present in an amount from 0.1 to 10 wt. %. In another embodiment, the catalyst comprises a combination of two or more metals on a support. Specific preferred metal compositions for various catalysts of this embodiment of the invention are provided below in Table 1. Where the catalyst comprises a first metal and a second metal, the first metal preferably is present in an amount from 0.1 to 5 wt. % and the second metal preferably is present in an amount from 0.1 to 5 wt. %. Where the catalyst comprises a first metal, a second metal and a third metal, the first metal preferably is present in an amount from 0.1 to 5 wt. %, the second metal preferably is present in an amount from 0.1 to 5 wt. %, and the third metal preferably is present in an amount from 0.1 to 2 wt. %. In one exemplary embodiment, the first metal is platinum and is present in an amount from 0.1 to 5 wt. %, the second metal is present in an amount from 0.1 to 5 wt. %, and the third metal, if present, preferably is present in an amount from 0.05 to 2 wt. %.

TABLE 1

EXEMPLARY METAL COMBINATIONS FOR CATALYSTS

| First Metal | Second Metal | Third Metal |
|---|---|---|
| Cu | Ag | |
| Cu | Cr | |
| Cu | V | |
| Cu | W | |
| Cu | Zn | |
| Ni | Au | |
| Ni | Re | |
| Ni | V | |
| Ni | W | |
| Pd | Co | |
| Pd | Cr | |
| Pd | Cu | |
| Pd | Fe | |
| Pd | La | |
| Pd | Mo | |
| Pd | Ni | |
| Pd | Re | |
| Pd | Sn | |
| Pd | V | |
| Pd | W | |
| Pt | Co | |
| Pt | Cr | |
| Pt | Cu | |
| Pt | Fe | |
| Pt | Mo | |
| Pt | Sn | |
| Pt | Sn | Co |
| Pt | Sn | Re |
| Pt | Sn | Ru |
| Pt | Sn | Pd |
| Rh | Cu | |
| Rh | Ni | |
| Ru | Co | |
| Ru | Cr | |
| Ru | Cu | |
| Ru | Fe | |
| Ru | La | |
| Ru | Mo | |
| Ru | Ni | |
| Ru | Sn | |

In another aspect, the catalyst composition may be represented by the formula:

$$Pt_v Pd_w Re_x Sn_y Ca_p Si_q O_r,$$

wherein: (i) the ratio of v:y is between 3:2 and 2:3; and/or (ii) the ratio of w:x is between 1:3 and 1:5. Thus, in this embodiment, the catalyst may comprise (i) platinum and tin; (ii) palladium and rhenium; or (iii) platinum, tin, palladium and rhenium. p and q preferably are selected such that p:q is from 1:20 to 1:200 with r being selected to satisfy valence requirements and v and w being selected such that:

$$0.005 \leq \frac{(3.25v + 1.75w)}{q} \leq 0.05$$

In this aspect, the process conditions and values of v, w, x, y, p, q, and r are preferably chosen such that at least 70% of the acetic acid, e.g., at least 80% or at least 90%, that is converted is converted to a compound selected from the group consisting of ethanol and ethyl acetate while less than 4% of the acetic acid is converted to alkanes. More preferably, the process conditions and values of v, w, x, y, p, q, and r are preferably chosen such that at least 70% of the acetic acid, e.g., at least 80% or at least 90%, that is converted is converted to ethanol, while less than 4% of the acetic acid is converted to alkanes. In many embodiments of the present invention, p is selected, in view of any minor impurities present, to ensure that the surface of the support is essentially free of active Brønsted acid sites.

In another aspect, the composition of the catalyst comprises:

$$Pt_v Pd_w Re_x Sn_y Al_z Ca_p Si_q O_r,$$

wherein: (i) v and y are between 3:2 and 2:3; and/or (ii) w and x are between 1:3 and 1:5. p and z and the relative locations of aluminum and calcium atoms present preferably are controlled such that Brønsted acid sites present upon the surface thereof are balanced by the support modifier, e.g., calcium metasilicate comprising crystalline calcium metasilicate at least in part; p and q are selected such that p:q is from 1:20 to 1:200 with r being selected to satisfy valence requirements and v and w are selected such that:

$$0.005 \leq \frac{(3.25v + 1.75w)}{q} \leq 0.05$$

Preferably, in this aspect, the catalyst has a surface area of at least about 100 m²/g, e.g., at least about 150 m²/g, at least about 200 m²/g or most preferably at least about 250 m²/g, and z and p≥z. In many embodiments of the present invention, p is selected, in view of any minor impurities present, to also ensure that the surface of the support is substantially free of active Brønsted acid sites which seem to facilitate conversion of ethanol into ethyl acetate. Thus, as with the previous embodiment, the process conditions and values of v, w, x, y, p, q, and r preferably are chosen such that at least 70% of the acetic acid, e.g., at least 80% or at least 90%, that is converted is converted to ethanol, while less than 4% of the acetic acid is converted to alkanes.

The catalyst compositions of the invention preferably are formed through metal impregnation of the modified support, although other processes such as chemical vapor deposition may also be employed. Before the metals are impregnated, it typically is desired to form the modified support, for example, through a step of impregnating the support material with the support modifier. A precursor to the support modifier, such as an acetate or a nitrate, may be used. In one aspect, the support modifier, e.g., crystalline CaSiO₃, at least in part, is added to the support material, e.g., SiO$_2$. For example, an aqueous suspension of the support modifier may be formed by adding the solid support modifier to deionized water, followed by the addition of colloidal support material thereto. The resulting mixture may be stirred and added to additional support material using, for example, incipient wetness techniques in which the support modifier is added to a support material having the same pore volume as the volume of the support modifier solution. Capillary action then draws the support modifier into the pores in the support material. The modified support can then be formed by drying and calcining to drive off water and any volatile components within the support modifier solution and depositing the support modifier on the support material. Drying may occur, for example, at a temperature of from 50° C. to 300° C., e.g., from 100° C. to 200° C. or about 120° C., optionally for a period of from 1 to 24 hours, e.g., from 3 to 15 hours or from 6 to 12 hours. Once formed, the modified supports may be shaped into particles having the desired size distribution, e.g., to form particles having an average particle size in the range of from 0.2 to 0.4 cm. The supports may be extruded, pelletized, tabletized, pressed, crushed or sieved to the desired size distribution. Any of the known methods to shape the support materials into desired size distribution can be employed. Calcining of the shaped modified support may occur, for example, at a temperature of from 250° C. to 800° C., e.g., from 300 to 700° C. or about 500° C., optionally for a period of from 1 to 12 hours, e.g., from 2 to 10 hours, from 4 to 8 hours or about 6 hours.

In a preferred method of preparing the catalyst, the metals are impregnated onto the modified support. A precursor of the first metal (first metal precursor) preferably is used in the metal impregnation step, such as a water soluble compound or water dispersible compound/complex that includes the first metal of interest. Depending on the metal precursor employed, the use of a solvent, such as water, glacial acetic acid or an organic solvent, may be preferred. The second metal also preferably is impregnated into the modified support from a second metal precursor. If desired, a third metal or third metal precursor may also be impregnated into the modified support.

Impregnation occurs by adding, optionally drop wise, either or both the first metal precursor and/or the second metal precursor and/or additional metal precursors, preferably in suspension or solution, to the dry modified support. The resulting mixture may then be heated, e.g., optionally under vacuum, in order to remove the solvent. Additional drying and calcining may then be performed, optionally with ramped heating to form the final catalyst composition. Upon heating and/or the application of vacuum, the metal(s) of the metal precursor(s) preferably decompose into their elemental (or oxide) form. In some cases, the completion of removal of the liquid carrier, e.g., water, may not take place until the catalyst is placed into use and calcined, e.g., subjected to the high temperatures encountered during operation. During the calcination step, or at least during the initial phase of use of the catalyst, such compounds are converted into a catalytically active form of the metal or a catalytically active oxide thereof.

Impregnation of the first and second metals (and optional additional metals) into the modified support may occur simultaneously (co-impregnation) or sequentially. In simultaneous impregnation, the first and second metal precursors (and optionally additional metal precursors) are mixed together and added to the modified support together, followed by drying and calcination to form the final catalyst composition. With simultaneous impregnation, it may be desired to employ a dispersion agent, surfactant, or solubilizing agent, e.g., ammonium oxalate, to facilitate the dispersing or solubilizing of the first and second metal precursors in the event the two precursors are incompatible with the desired solvent, e.g., water.

In sequential impregnation, the first metal precursor is first added to the modified support followed by drying and calcining, and the resulting material is then impregnated with the second metal precursor followed by an additional drying and calcining step to form the final catalyst composition. Additional metal precursors (e.g., a third metal precursor) may be added either with the first and/or second metal precursor or an a separate third impregnation step, followed by drying and calcination. Of course, combinations of sequential and simultaneous impregnation may be employed if desired.

Suitable metal precursors include, for example, metal halides, amine solubilized metal hydroxides, metal nitrates or metal oxalates. For example, suitable compounds for platinum precursors and palladium precursors include chloroplatinic acid, ammonium chloroplatinate, amine solubilized platinum hydroxide, platinum nitrate, platinum tetra ammonium nitrate, platinum chloride, platinum oxalate, palladium nitrate, palladium tetra ammonium nitrate, palladium chloride, palladium oxalate, sodium palladium chloride, and sodium platinum chloride. Generally, both from the point of view of economics and environmental aspects, aqueous solutions of soluble compounds of platinum are preferred. In one embodiment, the first metal precursor is not a metal halide and is substantially free of metal halides. Without being bound to theory, such non-(metal halide) precursors are believed to increase selectivity to ethanol. A particularly preferred precursor to platinum is platinum ammonium nitrate, Pt(NH$_3$)$_4$(NO$_4$)$_2$.

In one aspect, the "promoter" metal or metal precursor is first added to the modified support, followed by the "main" or "primary" metal or metal precursor. Of course the reverse order of addition is also possible. Exemplary precursors for promoter metals include metal halides, amine solubilized metal hydroxides, metal nitrates or metal oxalates. As indicated above, in the sequential embodiment, each impregnation step preferably is followed by drying and calcination. In the case of promoted bimetallic catalysts as described above, a sequential impregnation may be used, starting with the addition of the promoter metal followed by a second impregnation step involving co-impregnation of the two principal metals, e.g., Pt and Sn.

As an example, PtSnICaSiO$_3$ on SiO$_2$ may be prepared by a first impregnation of CaSiO$_3$, e.g., crystalline CaSiO$_3$, onto the SiO$_2$, followed by the co-impregnation with Pt(NH$_3$)$_4$(NO$_4$)$_2$ and Sn(AcO)$_2$. Again, each impregnation step may be followed by drying and calcination steps. In most cases, the impregnation may be carried out using metal nitrate solutions. However, various other soluble salts, which upon calcination release metal ions, can also be used. Examples of other suitable metal salts for impregnation include, metal acids, such as perrhenic acid solution, metal oxalates, and the like. In those cases where substantially pure ethanol is to be produced, it is generally preferable to avoid the use of halogenated precursors for the platinum group metals, using the nitrogenous amine and/or nitrate based precursors instead.

The process of hydrogenating acetic acid to form ethanol according to one embodiment of the invention may be conducted in a variety of configurations using a fixed bed reactor or a fluidized bed reactor as one of skill in the art will readily appreciate. In many embodiments of the present invention, an "adiabatic" reactor can be used; that is, there is little or no need for internal plumbing through the reaction zone to add or remove heat. Alternatively, a shell and tube reactor provided with a heat transfer medium can be used. In many cases, the reaction zone may be housed in a single vessel or in a series of vessels with heat exchangers therebetween. It is considered significant that acetic acid reduction processes using the catalysts of the present invention may be carried out in adiabatic reactors as this reactor configuration is typically far less capital intensive than tube and shell configurations.

Typically, the catalyst is employed in a fixed bed reactor, e.g., in the shape of an elongated pipe or tube where the reactants, typically in the vapor form, are passed over or through the catalyst. Other reactors, such as fluid or ebullient bed reactors, can be employed, if desired. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably the reaction is carried out in the vapor phase under the following conditions. The reaction temperature may the range from of 125° C. to 350° C., e.g., from 200° C. to 325° C., from 225° C. to about 300° C., or from 250° C. to about 300° C. The pressure may range from 10 KPa to 3000 KPa (about 0.1 to 30 atmospheres), e.g., from 50 KPa to 2300 KPa, or from 100 KPa to 1500 KPa. The reactants may be fed to the reactor at a gas hourly space velocities (GHSV) of greater than 500 $hr^{-1}$, e.g., greater than 1000 $hr^{-1}$, greater than 2500 $hr^{-1}$ and even greater than 5000 $hr^{-1}$. In terms of ranges the GHSV may range from 50 $hr^{-1}$ to 50,000 $hr^{-1}$, e.g., from 500 $hr^{-1}$ to 30,000 $hf^{-1}$, from 1000 $hf^{-1}$ to 10,000 $hr^{-1}$, or from 1000 $hf^{-1}$ to 6500 $hf^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 4:1, e.g., greater than 5:1 or greater than 10:1.

Contact or residence time can also vary widely, depending upon such variables as amount of acetic acid, catalyst, reactor, temperature and pressure. Typical contact times range from a fraction of a second to more than several hours when a catalyst system other than a fixed bed is used, with preferred contact times, at least for vapor phase reactions, from 0.1 to 100 seconds, e.g., from 0.3 to 80 seconds or from 0.4 to 30 seconds.

The acetic acid may be vaporized at the reaction temperature, and then the vaporized acetic acid can be fed along with hydrogen in undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid.

In particular, using catalysts of the present invention may achieve favorable conversion of acetic acid and favorable selectivity and productivity to ethanol. For purposes of the present invention, the term conversion refers to the amount of acetic acid in the feed that is convert to a compound other than acetic acid. Conversion is expressed as a mole percentage based on acetic acid in the feed. The conversion of acetic acid (AcOH) is calculated from gas chromatography (GC) data using the following equation:

$$AcOH\ Conv.\ (\%) = 100 * \frac{\text{mmol AcOH(feed stream)} - \text{mmol AcOH}(GC)}{\text{mmol AcOH(feed stream)}}$$

For purposes of the present invention, the conversion may be at least 10%, e.g., at least 20%, at least 40%, at least 50%, at least 60%, at least 70% or at least 80%. Although catalysts that have high conversions are desirable, such as at least 80% or at least 90%, a low conversion may be acceptable at high selectivity for ethanol. It is, of course, well understood that in many cases, it is possible to compensate for conversion by appropriate recycle streams or use of larger reactors, but it is more difficult to compensate for poor selectivity.

"Selectivity" is expressed as a mole percent based on converted acetic acid. It should be understood that each compound converted from acetic acid has an independent selectivity and that selectivity is independent from conversion. For example, if 50 mole % of the converted acetic acid is converted to ethanol, we refer to the ethanol selectivity as 50%. Selectivity to ethanol (EtOH) is calculated from gas chromatography (GC) data using the following equation:

$$EtOH\ Sel.\ (\%) = 100 * \frac{\text{mmol EtOH}(GC)}{\frac{\text{Total mmol C}(GC)}{2} - \text{mmol AcOH(feed stream)}}$$

wherein "Total mmol C (GC)" refers to total mmols of carbon from all of the products analyzed by gas chromatograph.

For purposes of the present invention, the selectivity to ethoxylates of the catalyst is at least 60%, e.g., at least 70%, or at least 80%. As used herein, the term "ethoxylates" refers specifically to the compounds ethanol, acetaldehyde, and ethyl acetate. Preferably, the selectivity to ethanol is at least 80%, e.g., at least 85% or at least 88%. In embodiments of the present invention is also desirable to have low selectivity to undesirable products, such as methane, ethane, and carbon dioxide. The selectivity to these undesirable products is less than 4%, e.g., less than 2% or less than 1%. Preferably, no detectable amounts of these undesirable products are formed during hydrogenation. In several embodiments of the present invention, formation of alkanes is low, usually under 2%, often under 1%, and in many cases under 0.5% of the acetic acid passed over the catalyst is converted to alkanes, which have little value other than as fuel.

Productivity refers to the grams of a specified product, e.g., ethanol, formed during the hydrogenation based on the kilogram of catalyst used per hour. In one embodiment of the present invention, a productivity of at least 500 grams of ethanol per kilogram catalyst per hour, e.g., at least 600 g/kg/hr, at least 700 g/kg/hr, at least 750 g/kg/hr, at least 800 g/kg/hr, at least 850 g/kg/hr, at least 900 g/kg/hr, or at least 1,000 g/kg/hr. In terms of ranges, the productivity preferably is from 500 to 3,000 grams of ethanol per kilogram catalyst per hour, e.g., from 700 to 2,500 or from 750 to 2,000.

Some catalysts of the present invention may achieve a conversion of acetic acid of at least 10%, a selectivity to ethanol of at least 80%, and a productivity of at least 200 g of ethanol per kg of catalyst per hour. A subset of catalysts of the invention may achieve a conversion of acetic acid of at least 50%, a selectivity to ethanol of at least 80%, a selectivity to undesirable compounds of less than 4%, and a productivity of at least 600 g of ethanol per kg of catalyst per hour.

The raw materials used in the hydrogenation process may be derived from any suitable source including natural gas, petroleum, coal, biomass and so forth. It is well known to produce acetic acid through methanol carbonylation, acetaldehyde oxidation, ethylene oxidation, oxidative fermentation, and anaerobic fermentation. As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive compared to natural gas, it may become advantageous to produce acetic acid from synthesis gas ("syn gas") that is derived from any available carbon source. U.S. Pat. No. 6,232,352, the disclosure of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syn gas is diverted from the methanol synthesis loop and supplied to a separator unit to recover CO and hydrogen, which are then used to produce acetic acid. In addition to acetic acid, the process can also be used to make hydrogen which may be utilized in connection with this invention.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syn gas is converted to methanol which may be carbonylated to acetic acid. The method likewise produces hydrogen which may be used in connection with this invention as noted above. U.S. Pat. No. 5,821,111, as well as U.S. Pat. No. 6,685,754, discloses a process for converting waste biomass through gasification into synthesis gas, the disclosures of which are incorporated herein by reference.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the ethanol synthesis reaction zones of the present invention without the need for condensing the acetic acid and light ends or removing water, saving overall processing costs.

Ethanol obtained from hydrogenation processes using the catalysts of the invention may be used in its own right as a fuel or subsequently converted to ethylene which is an important commodity feedstock as it can be converted to polyethylene, vinyl acetate and/or ethyl acetate or any of a wide variety of other chemical products. For example, ethylene can also be converted to numerous polymer and monomer products. The dehydration of ethanol to ethylene is shown below.

Any of known dehydration catalysts can be employed in to dehydrate ethanol, such as those described in U.S. Pub. Nos. 2010/0030001 and 2010/0030002, the entire contents and disclosures of which are hereby incorporated by reference. A zeolite catalyst, for example, may be employed as the dehydration catalyst. While any zeolite having a pore diameter of at least about 0.6 nm can be used, preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated by reference.

Ethanol may also be used as a fuel, in pharmaceutical products, cleansers, sanitizers, hydrogenation transport or consumption. Ethanol may also be used as a source material for making ethyl acetate, aldehydes, and higher alcohols, especially butanol. In addition, any ester, such as ethyl acetate, formed during the process of making ethanol according to the present invention may be further reacted with an acid catalyst to form additional ethanol as well as acetic acid, which may be recycled to the hydrogenation process.

The invention is described in detail below with reference to numerous embodiments for purposes of exemplification and illustration only. Modifications to particular embodiments within the spirit and scope of the present invention, set forth in the appended claims, will be readily apparent to those of skill in the art.

The following examples describe the procedures used for the preparation of various catalysts employed in the process of this invention.

EXAMPLES

Figure 3:
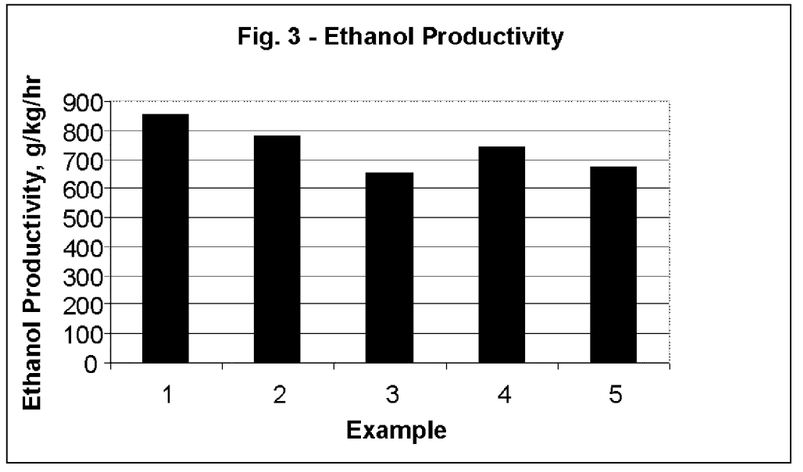
FIG. 3 is a graph of the productivity of ethanol of the catalysts in Examples 1-5.

First, five Pt/Sn catalysts were formed, each having the same Pt/Sn loadings and ratios on $CaSiO_3$ modified $SiO_2$ supports. The resulting catalysts were then tested in the hydrogenation of acetic acid in Examples 1-5, and ethanol productivity was determined. The $SiO_2$ support used in Example 1 was modified with a crystalline $CaSiO_3$ (about 2-5% crystallinity), while the supports of Examples 2-5 were modified with amorphous $CaSiO_3$. The reaction feed liquid of acetic acid was evaporated and charged to the reactor along with hydrogen and helium as a carrier gas. The resultant ethanol productivities are shown in FIG. 3.

As shown, Example 1, which utilized a $CaSiO_3$ comprising crystalline $CaSiO_3$ surprisingly and unexpectedly demonstrated superior ethanol productivity of 850 g/kg/hr. In comparison, Examples 2-5, all of which utilized conventional amorphous $CaSiO_3$ demonstrated at most 780 g/kg/hr ethanol productivity. This is an ethanol productivity increase of about 10% over the conventional modified supported catalysts.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing ethanol, comprising hydrogenating acetic acid in the presence of a catalyst comprising a first metal, a silicaceous support, and at least one metasilicate support modifier, wherein at least 0.5 wt. % of the metasilicate support modifier is in a crystalline phase, as determined by XRD.

2. The process of claim 1, wherein from 0.5 wt. % to 5 wt. % of the metasilicate support modifier is in a crystalline phase.

3. The process of claim 1, wherein at least 1 wt. % of the metasilicate support modifier is in a crystalline phase.

4. The process of claim 1, wherein the first metal is present in an amount of from 0.1 to 25 wt. %, based on the total weight of the catalyst and the first metal is selected from the group consisting of copper, iron, cobalt, nickel, ruthenium, rhodium, palladium, osmium, iridium, platinum, titanium, zinc, chromium, rhenium, molybdenum, and tungsten.

5. The process of claim 4, wherein the catalyst further comprises a second metal different from the first metal, wherein the second metal is present in an amount of from 0.1 to 10 wt. %, based on the total weight of the catalyst and the second metal is selected from the group consisting of copper, molybdenum, tin, chromium, iron, cobalt, vanadium, tungsten, palladium, platinum, lanthanum, cerium, manganese, ruthenium, rhenium, gold, and nickel.

6. The process of claim 1, wherein the at least one metasilicate support modifier is selected from the group consisting of metasilicates of sodium, potassium, magnesium, calcium, scandium, yttrium, and zinc.

7. The process of claim 1, wherein the at least one metasilicate support modifier is present in an amount of 0.1 wt. % to 50 wt. %, based on the total weight of the catalyst.

8. The process of claim 1, wherein the siliceous support is present in an amount of 25 wt. % to 99 wt. %, based on the total weight of the catalyst.

9. The process of claim 1, wherein the siliceous support is selected from the group consisting of silica, silica/alumina, calcium metasilicate, pyrogenic silica, high purity silica and mixtures thereof.

* * * * *